United States Patent
Weingarten et al.

(10) Patent No.: US 10,314,564 B2
(45) Date of Patent: *Jun. 11, 2019

(54) COMPUTED TOMOGRAPHY ENHANCED FLUOROSCOPIC SYSTEM, DEVICE, AND METHOD OF UTILIZING THE SAME

(71) Applicant: Covidien LP, Mansfield, MA (US)

(72) Inventors: Oren P. Weingarten, Herzliya (IL); Dorian Averbuch, Ramat Hasharon (IL)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/972,159

(22) Filed: May 6, 2018

(65) Prior Publication Data
US 2018/0296198 A1 Oct. 18, 2018

Related U.S. Application Data

(63) Continuation of application No. 14/880,361, filed on Oct. 12, 2015, now Pat. No. 9,986,983.
(Continued)

(51) Int. Cl.
*A61B 34/10* (2016.01)
*A61B 10/04* (2006.01)
(Continued)

(52) U.S. Cl.
CPC ............... *A61B 10/04* (2013.01); *A61B 6/03* (2013.01); *A61B 6/032* (2013.01); *A61B 6/12* (2013.01);
(Continued)

(58) Field of Classification Search
CPC .......... A61B 10/04; A61B 34/10; A61B 34/20
See application file for complete search history.

(56) References Cited

U.S. PATENT DOCUMENTS 5,852,646 A    12/1998   Klotz et al.
5,930,329 A    7/1999    Navab
(Continued)

FOREIGN PATENT DOCUMENTS

CN    1503184 A     6/2004
CN    103260518 A   8/2013
(Continued)

OTHER PUBLICATIONS

International Search Report and Written Opinion from PCT Appl. No. PCT/US2015/056376 dated Jan. 26, 2016.
(Continued)

*Primary Examiner* — Rochelle D Turchen

(57) ABSTRACT

A system for enhanced surgical navigation including a computing device and an imaging device. The computing device is configured to import a navigation path to a target using a first data set of computed tomography images previously acquired, display the navigation path on a graphical user interface for navigation to the target and placement of a plurality of markers in tissue proximate the target, and acquire a second data set of computed tomography images including the plurality of markers. The imaging device is configured to capture fluoroscopic data of tissue proximate the plurality of markers. The computing device is further configured to register the fluoroscopic data to the second data set of computed tomography images based on marker position and marker orientation within the fluoroscopic data and marker position and orientation within the second data set of computed tomography images.

16 Claims, 7 Drawing Sheets

Related U.S. Application Data

(60) Provisional application No. 62/073,287, filed on Oct. 31, 2014, provisional application No. 62/073,306, filed on Oct. 31, 2014.

(51) Int. Cl.

| | | |
|---|---|---|
| *A61B 6/03* | (2006.01) | |
| *A61B 6/00* | (2006.01) | |
| *A61B 6/12* | (2006.01) | |
| *A61B 34/20* | (2016.01) | |
| *A61B 18/00* | (2006.01) | |
| *A61B 18/18* | (2006.01) | |
| *A61B 90/00* | (2016.01) | |

(52) U.S. Cl.
CPC .............. *A61B 6/463* (2013.01); *A61B 6/487* (2013.01); *A61B 6/5235* (2013.01); *A61B 34/10* (2016.02); *A61B 34/20* (2016.02); *A61B 6/461* (2013.01); *A61B 6/58* (2013.01); *A61B 2018/00577* (2013.01); *A61B 2018/1861* (2013.01); *A61B 2034/107* (2016.02); *A61B 2034/2051* (2016.02); *A61B 2090/364* (2016.02); *A61B 2090/376* (2016.02); *A61B 2090/3762* (2016.02); *A61B 2090/3966* (2016.02); *A61B 2090/3987* (2016.02)

(56) References Cited

U.S. PATENT DOCUMENTS

| | | | |
|---|---|---|---|
| 5,951,475 | A | 9/1999 | Gueziec et al. |
| 5,963,612 | A | 10/1999 | Navab |
| 5,963,613 | A | 10/1999 | Navab |
| 6,038,282 | A | 3/2000 | Wiesent et al. |
| 6,049,582 | A | 4/2000 | Navab |
| 6,050,724 | A | 4/2000 | Schmitz et al. |
| 6,055,449 | A | 4/2000 | Navab |
| 6,081,577 | A | 6/2000 | Webber |
| 6,120,180 | A | 9/2000 | Graumann |
| 6,236,704 | B1 | 5/2001 | Navab et al. |
| 6,314,310 | B1 | 11/2001 | Ben-Haim et al. |
| 6,317,621 | B1 | 11/2001 | Graumann et al. |
| 6,351,513 | B1 | 2/2002 | Bani-Hashemi et al. |
| 6,389,104 | B1 | 5/2002 | Bani-Hashemi et al. |
| 6,404,843 | B1 | 6/2002 | Vaillant |
| 6,424,731 | B1 | 7/2002 | Launay et al. |
| 6,470,207 | B1 | 10/2002 | Simon et al. |
| 6,484,049 | B1 | 11/2002 | Seeley et al. |
| 6,485,422 | B1 | 11/2002 | Mikus et al. |
| 6,490,475 | B1 | 12/2002 | Seeley et al. |
| 6,491,430 | B1 | 12/2002 | Seissler |
| 6,535,756 | B1 | 3/2003 | Simon et al. |
| 6,539,127 | B1 | 3/2003 | Roche et al. |
| 6,546,068 | B1 | 4/2003 | Shimura |
| 6,546,279 | B1 | 4/2003 | Bova et al. |
| 6,549,607 | B1 | 4/2003 | Webber |
| 6,697,664 | B2 | 2/2004 | Kienzle, III et al. |
| 6,707,878 | B2 | 3/2004 | Claus et al. |
| 6,714,810 | B2 | 3/2004 | Grzeszczuk et al. |
| 6,725,080 | B2 | 4/2004 | Melkent et al. |
| 6,731,283 | B1 | 5/2004 | Navab |
| 6,731,970 | B2 | 5/2004 | Schlossbauer et al. |
| 6,768,784 | B1 | 7/2004 | Green et al. |
| 6,782,287 | B2 | 8/2004 | Grzeszczuk et al. |
| 6,785,356 | B2 | 8/2004 | Grass et al. |
| 6,785,571 | B2 | 8/2004 | Glossop |
| 6,801,597 | B2 | 10/2004 | Webber |
| 6,823,207 | B1 | 11/2004 | Jensen et al. |
| 6,856,826 | B2 | 2/2005 | Seeley et al. |
| 6,856,827 | B2 | 2/2005 | Seeley et al. |
| 6,865,253 | B2 | 3/2005 | Blumhofer et al. |
| 6,898,263 | B2 | 5/2005 | Avinash et al. |
| 6,944,260 | B2 | 9/2005 | Hsieh et al. |
| 6,956,927 | B2 | 10/2005 | Sukeyasu et al. |
| 7,010,080 | B2 | 3/2006 | Mitschke et al. |
| 7,010,152 | B2 | 3/2006 | Bojer et al. |
| 7,035,371 | B2 | 4/2006 | Boese et al. |
| 7,106,825 | B2 | 9/2006 | Gregerson et al. |
| 7,117,027 | B2 | 10/2006 | Zheng et al. |
| 7,129,946 | B2 | 10/2006 | Ditt et al. |
| 7,130,676 | B2 | 10/2006 | Barrick |
| 7,165,362 | B2 | 1/2007 | Jobs et al. |
| 7,251,522 | B2 | 7/2007 | Essenreiter et al. |
| 7,327,872 | B2 | 2/2008 | Vaillant et al. |
| 7,343,195 | B2 | 3/2008 | Strommer et al. |
| 7,356,367 | B2 | 4/2008 | Liang et al. |
| 7,369,641 | B2 | 5/2008 | Tsubaki et al. |
| 7,440,538 | B2 | 10/2008 | Tsujii |
| 7,467,007 | B2 | 12/2008 | Lothert |
| 7,474,913 | B2 | 1/2009 | Durlak |
| 7,499,743 | B2 | 3/2009 | Vass et al. |
| 7,502,503 | B2 | 3/2009 | Bojer et al. |
| 7,505,549 | B2 | 3/2009 | Ohishi et al. |
| 7,508,388 | B2 | 3/2009 | Barfuss et al. |
| 7,603,155 | B2 | 10/2009 | Jensen |
| 7,620,223 | B2 | 11/2009 | Xu et al. |
| 7,639,866 | B2 | 12/2009 | Pomero et al. |
| 7,664,542 | B2 | 2/2010 | Boese et al. |
| 7,689,019 | B2 | 3/2010 | Boese et al. |
| 7,689,042 | B2 | 3/2010 | Brunner et al. |
| 7,693,263 | B2 | 4/2010 | Bouvier et al. |
| 7,697,972 | B2 | 4/2010 | Verard et al. |
| 7,711,082 | B2 | 5/2010 | Fujimoto et al. |
| 7,711,083 | B2 | 5/2010 | Heigl et al. |
| 7,711,409 | B2 | 5/2010 | Keppel et al. |
| 7,720,520 | B2 | 5/2010 | Willis |
| 7,725,165 | B2 | 5/2010 | Chen et al. |
| 7,734,329 | B2 | 6/2010 | Boese et al. |
| 7,742,557 | B2 | 6/2010 | Brunner et al. |
| 7,761,135 | B2 | 7/2010 | Pfister et al. |
| 7,778,685 | B2 | 8/2010 | Evron et al. |
| 7,787,932 | B2 | 8/2010 | Vilsmeier et al. |
| 7,804,991 | B2 | 9/2010 | Abovitz et al. |
| 7,831,096 | B2 | 11/2010 | Williamson, Jr. |
| 7,835,779 | B2 | 11/2010 | Anderson et al. |
| 7,853,061 | B2 | 12/2010 | Gorges et al. |
| 7,877,132 | B2 | 1/2011 | Rongen et al. |
| 7,899,226 | B2 | 3/2011 | Pescatore et al. |
| 7,907,989 | B2 | 3/2011 | Borgert et al. |
| 7,912,180 | B2 | 3/2011 | Zou et al. |
| 7,912,262 | B2 | 3/2011 | Timmer et al. |
| 7,949,088 | B2 | 5/2011 | Nishide et al. |
| 7,991,450 | B2 | 8/2011 | Virtue et al. |
| 7,995,819 | B2 | 8/2011 | Vaillant et al. |
| 8,000,436 | B2 | 8/2011 | Seppi et al. |
| 8,043,003 | B2 | 10/2011 | Vogt et al. |
| 8,045,780 | B2 | 10/2011 | Boese et al. |
| 8,050,739 | B2 | 11/2011 | Eck et al. |
| 8,090,168 | B2 | 1/2012 | Washburn et al. |
| 8,098,914 | B2 | 1/2012 | Liao et al. |
| 8,111,894 | B2 | 2/2012 | Van De Haar |
| 8,111,895 | B2 | 2/2012 | Spahn |
| 8,126,111 | B2 | 2/2012 | Uhde et al. |
| 8,126,241 | B2 | 2/2012 | Zarkh et al. |
| 8,150,131 | B2 | 4/2012 | Harer et al. |
| 8,180,132 | B2 | 5/2012 | Gorges et al. |
| 8,195,271 | B2 | 6/2012 | Rahn |
| 8,200,316 | B2 | 6/2012 | Keppel et al. |
| 8,208,708 | B2 | 6/2012 | Homan et al. |
| 8,218,843 | B2 | 7/2012 | Edlauer et al. |
| 8,229,061 | B2 | 7/2012 | Hanke et al. |
| 8,238,625 | B2 | 8/2012 | Strommer et al. |
| 8,248,413 | B2 | 8/2012 | Gattani et al. |
| 8,270,691 | B2 | 9/2012 | Xu et al. |
| 8,271,068 | B2 | 9/2012 | Khamene et al. |
| 8,275,448 | B2 | 9/2012 | Camus et al. |
| 8,295,577 | B2 | 10/2012 | Zarkh et al. |
| 8,306,303 | B2 | 11/2012 | Bruder et al. |
| 8,311,617 | B2 | 11/2012 | Keppel et al. |
| 8,320,992 | B2 | 11/2012 | Frenkel et al. |
| 8,340,379 | B2 | 12/2012 | Razzaque et al. |
| 8,345,817 | B2 | 1/2013 | Fuchs et al. |
| 8,346,344 | B2 | 1/2013 | Pfister et al. |

(56) References Cited

U.S. PATENT DOCUMENTS

| | | |
|---|---|---|
| 8,358,874 B2 | 1/2013 | Haras |
| 8,374,416 B2 | 2/2013 | Gagesch et al. |
| 8,374,678 B2 | 2/2013 | Graumann |
| 8,423,117 B2 | 4/2013 | Pichon et al. |
| 8,442,618 B2 | 5/2013 | Strommer et al. |
| 8,515,527 B2 | 8/2013 | Vaillant et al. |
| 8,526,688 B2 | 9/2013 | Groszmann et al. |
| 8,526,700 B2 | 9/2013 | Isaacs |
| 8,532,258 B2 | 9/2013 | Bulitta et al. |
| 8,532,259 B2 | 9/2013 | Shedlock et al. |
| 8,548,567 B2 | 10/2013 | Maschke et al. |
| 8,625,865 B2 | 1/2014 | Zarkh et al. |
| 8,625,869 B2 | 1/2014 | Harder et al. |
| 8,666,137 B2 | 3/2014 | Nielsen et al. |
| 8,670,603 B2 | 3/2014 | Tolkowsky et al. |
| 8,675,996 B2 | 3/2014 | Liao et al. |
| 8,693,622 B2 | 4/2014 | Graumann et al. |
| 8,693,756 B2 | 4/2014 | Tolkowsky et al. |
| 8,694,075 B2 | 4/2014 | Groszmann et al. |
| 8,706,186 B2 | 4/2014 | Fichtinger et al. |
| 8,712,129 B2 | 4/2014 | Strommer et al. |
| 8,718,346 B2 | 5/2014 | Isaacs et al. |
| 8,750,582 B2 | 6/2014 | Boese et al. |
| 8,755,587 B2 | 6/2014 | Bender et al. |
| 8,781,064 B2 | 7/2014 | Fuchs et al. |
| 8,792,704 B2 | 7/2014 | Isaacs |
| 8,798,339 B2 | 8/2014 | Mielekamp et al. |
| 8,831,310 B2 | 9/2014 | Razzaque et al. |
| 8,855,748 B2 | 10/2014 | Keppel et al. |
| 9,001,121 B2 | 4/2015 | Finlayson et al. |
| 9,001,962 B2 | 4/2015 | Funk |
| 9,008,367 B2 | 4/2015 | Tolkowsky et al. |
| 9,031,188 B2 | 5/2015 | Belcher et al. |
| 9,036,777 B2 | 5/2015 | Ohishi et al. |
| 9,042,624 B2 | 5/2015 | Dennerlein |
| 9,044,190 B2 | 6/2015 | Rubner et al. |
| 9,087,404 B2 | 7/2015 | Hansis et al. |
| 9,095,252 B2 | 8/2015 | Popovic |
| 9,104,902 B2 | 8/2015 | Xu et al. |
| 9,111,175 B2 | 8/2015 | Strommer et al. |
| 9,135,706 B2 | 9/2015 | Zagorchev et al. |
| 9,171,365 B2 | 10/2015 | Mareachen et al. |
| 9,179,878 B2 | 11/2015 | Jeon |
| 9,216,065 B2 | 12/2015 | Cohen et al. |
| 9,232,924 B2 | 1/2016 | Liu et al. |
| 9,262,830 B2 | 2/2016 | Bakker et al. |
| 9,265,468 B2 | 2/2016 | Rai et al. |
| 9,277,893 B2 | 3/2016 | Tsukagoshi et al. |
| 9,280,837 B2 | 3/2016 | Grass et al. |
| 9,282,944 B2 | 3/2016 | Fallavollita et al. |
| 9,401,047 B2 | 7/2016 | Bogoni et al. |
| 9,406,134 B2 | 8/2016 | Klingenbeck-Regn |
| 9,445,772 B2 | 9/2016 | Callaghan |
| 9,445,776 B2 | 9/2016 | Han et al. |
| 9,466,135 B2 | 10/2016 | Koehler et al. |
| 9,974,525 B2 | 5/2018 | Weingarten et al. |
| 9,986,983 B2 | 6/2018 | Weingarten et al. |
| 2005/0027193 A1 | 2/2005 | Mitschke et al. |
| 2006/0033493 A1 | 2/2006 | Biglieri |
| 2006/0167416 A1* | 7/2006 | Mathis ............... A61B 10/0275 604/164.01 |
| 2008/0146916 A1 | 6/2008 | Okerlund |
| 2008/0243142 A1 | 10/2008 | Gildenberg |
| 2008/0269588 A1 | 10/2008 | Csavoy et al. |
| 2009/0137952 A1 | 5/2009 | Ramamurthy et al. |
| 2009/0257551 A1 | 10/2009 | Dafni et al. |
| 2010/0008475 A1 | 1/2010 | Maschke |
| 2012/0281903 A1 | 11/2012 | Trumer et al. |
| 2013/0317339 A1 | 11/2013 | Waldstreicher et al. |
| 2015/0227679 A1 | 8/2015 | Kamer et al. |
| 2016/0005194 A1 | 1/2016 | Schretter et al. |
| 2016/0206380 A1 | 7/2016 | Sparks et al. |
| 2016/0287343 A1 | 10/2016 | Eichler et al. |

FOREIGN PATENT DOCUMENTS

| | | |
|---|---|---|
| CN | 104050348 A | 9/2014 |
| EP | 1510182 A2 | 3/2005 |
| WO | 2005013841 A1 | 2/2005 |
| WO | 2006078678 A2 | 7/2006 |
| WO | 2007113703 A2 | 10/2007 |

OTHER PUBLICATIONS

Extended European Search Report from Appl. No. EP 15 854 370.2 dated Jun. 11, 2018 (8 pages).

Chinese Office Action issued in corresponding Appl. No. CN 201580060018.3 dated Dec. 28, 2018, together with English language translation (22 pages).

* cited by examiner

COMPUTED TOMOGRAPHY ENHANCED FLUOROSCOPIC SYSTEM, DEVICE, AND METHOD OF UTILIZING THE SAME

CROSS REFERENCE TO RELATED APPLICATION

The present application is a continuation of U.S. application Ser. No. 14/880,361, filed on Oct. 12, 2015, which claims the benefit of and priority to U.S. Provisional Applications Ser. No. 62/073,306 and 62/073,287, filed on Oct. 31, 2014. This application is related to U.S. patent application Ser. No. 14/880,338, filed on Oct. 12, 2015. The entire contents of each of the above are incorporated herein by reference.

BACKGROUND

Technical Field

The present disclosure relates to a system, apparatus, and method of navigation and position confirmation for surgical procedures. More particularly, the present disclosure relates to a system and method for enhanced navigation of an extended working channel or catheter and one or more medical instruments positionable therethrough in one or more branched luminal networks of a patient and confirming placement of those medical instruments prior to initiating treatment or biopsy.

Description of Related Art

Microwave ablation is a commonly applied method for treating various maladies affecting organs including the liver, brain, heart, lung and kidney. Commonly, one or more imaging modalities, whether magnetic resonance imaging, ultrasound imaging, computer tomography (CT), as well as others will be employed by a clinician to identify areas of interest within the patent and ultimately targets for treatment. Once identified, an area of interest will typically require a biopsy using a biopsy tool to confirm whether treatment and/or observation are necessitated at a particular time. This biopsy is typically performed under one of a number of image guidance modalities, and/or in conjunction with a navigation system. If the biopsy reveals that the area of interest is malignant, it may prove useful to treat the area using microwave ablation.

Microwave ablation may be performed by transmitting microwave energy through a needle inserted percutaneously in the patient to ablate the area of interest. Alternatively, where practicable, an endoscopic approach can be undertaken, where, once navigated to the identified target, a flexible microwave ablation catheter can be placed in the target to ablate the area of interest. The endoscopic approach is particularly useful when treating luminal networks of the body such as the lungs.

To enable the endoscopic approach, for example in the lungs, endobronchial navigation systems have been developed that use CT image data to create a navigation plan to facilitate advancing a navigation catheter (or other suitable device) through a bronchoscope and a branch of the bronchus of a patient to the area of interest. Endobronchial navigation may be employed both in the diagnostic (i.e., biopsy) phase and the treatment phases. Electromagnetic tracking may be utilized in conjunction with the CT data to facilitate guiding the navigation catheter through the branch of the bronchus to the area of interest. In certain instances, the navigation catheter may be positioned within one of the airways of the branched luminal networks adjacent to or within the area of interest to provide access for one or more medical instruments.

Once the navigation catheter is in position, fluoroscopy may be used to visualize medical instruments including biopsy tools, such as, for example, brushes, needles and forceps, as well as treatment tools such as an ablation catheter, as they are passed through the navigation catheter and into the lung and to the area of interest. Conventional fluoroscopy is widely used during medical procedures as a visualization imaging tool for guiding medical instruments inside the human body. Although medical instruments like catheters, biopsy tools, etc., are clearly visible on a fluoroscopic picture, organic features such as soft tissue, blood vessels, suspicious tumor lesions etc., are either somewhat or completely transparent and thus hard to identify with conventional fluoroscopy.

During procedures, such as a biopsy or ablation, a fluoroscopic image may be used by a clinician to aid in visualizing the placement of a medical instrument within a patient's body. However, although the medical instrument is visible in the fluoroscopic image, the area of interest or target tissue is generally somewhat transparent and not necessarily clearly visible within the image. Moreover, fluoroscopic images render flat 2D images on which it can be somewhat challenging to assess three-dimensional position of the medical instrument. As such, the clinician is not provided all the information that could be desired to visualize the placement of the medical device within the patient's body relative to the area of interest.

SUMMARY

As can be appreciated, a microwave ablation catheter that is positionable through one or more branched luminal networks of a patient to treat tissue may prove useful in the surgical arena.

Aspects of the present disclosure are described in detail with reference to the figures wherein like reference numerals identify similar or identical elements. As used herein, the term "distal" refers to the portion that is being described which is further from a user, while the term "proximal" refers to the portion that is being described which is closer to a user.

According to one aspect of the present disclosure, a system for enhanced surgical navigation is provided. The system includes a computing device and an imaging device. The computing device is configured to import a navigation path to a target using a first data set of computed tomography images previously acquired, display the navigation path on a graphical user interface for navigation to the target and placement of a plurality of markers in tissue proximate the target, and acquire a second data set of computed tomography images including the plurality of markers. The imaging device is configured to capture fluoroscopic data of tissue proximate the plurality of markers. The computing device is further configured to register the fluoroscopic data to the second data set of computed tomography images based on marker position and marker orientation within the fluoroscopic data and marker position and orientation within the second data set of computed tomography images.

The computing device may be further configured to display a representation of the second data set of computed tomography images on the graphical user interface, and display the fluoroscopic data on the graphical user interface. Additionally, the computing device may further be configured to receive a selection of at least a portion of the second data set of computed tomography images or the fluoroscopic data, combine the selection with at least one of the second data set of computed tomography images or the fluoroscopic data into a combined image, and display the combined image on the graphical user interface. Additionally, or alternatively, the computing device may be configured to combine at least a portion of the second data set of computed tomography images with the fluoroscopic data into a combined image, and display the combined image on the graphical user interface. The combined image may include at least one of a fused, superimposed, or overlaid image of at least a portion of the second data set of computed tomography images with the fluoroscopic data.

The fluoroscopic data may be real-time fluoroscopic video of tissue proximate the plurality of markers, a single image, or a plurality of images and may include a medical instrument positioned relative to tissue proximate the target and the computing device may be further configured to analyze the fluoroscopic data and determine whether the medical device is correctly positioned relative to the target. Additionally, the computing device may also be configured to acquire a second fluoroscopic data set of tissue proximate the plurality of markers from the imaging device from a second perspective such that a three-dimensional position of the medical instrument is viewable from a different angle. The computing device may further be configured to analyze the second fluoroscopic data to determine whether the three-dimensional position of the medical instrument relative to the target is correct.

The system may further include a second imaging device configured to capture second fluoroscopic data of the tissue proximate the plurality of markers from a different perspective that the first fluoroscopic data. Additionally, the system may further include a catheter guide assembly navigatable to the target using the navigation path, the catheter guide assembly including an extended working channel insertable into a working channel of a bronchoscope to access a luminal network. Additionally, or alternatively, the system may further include a biopsy device positionable through the extended working channel, the biopsy device configured to obtain a sample of tissue proximate the target. Additionally, or alternatively, the system may further include a microwave ablation device positionable through the extended working channel, the microwave ablation device configured to ablate tissue proximate the target.

In yet another aspect of the present disclosure a non-transitory computer readable storage medium is provided including instructions that when executed by a computing device, cause the computing device to plan a navigation path to a target using a first data set of computed tomography images previously acquired, navigate a marker placement device to the target using the navigation path, acquire a second data set of computed tomography images including a plurality of markers previously placed in tissue proximate the target, plan a second navigation path to a second target using the second data set of computed tomography images, navigate a medical instrument to the second target using the second navigation path, capture fluoroscopic data of tissue proximate the plurality of markers using a fluoroscope, and register the fluoroscopic data to the second data set of computed tomography images based on marker position and/or orientation within the fluoroscopic data and marker position and/or orientation within the second data set of computed tomography images.

The first target and the second target may identify substantially the same area of interest. A sample of the target, such as tissue proximate the target, may be retrieved for biopsy or other purposes. Additionally, the computing device may further display a representation of the second data set of computed tomography images and the fluoroscopic data on a graphical user interface. Further, at least a portion of the second data set of computed tomography images may be combined with the fluoroscopic data to generate a combined image for display on the graphical user interface. The combined image may be generated via superimposing, fusing, or overlaying the second data set of computed tomography images with the fluoroscopic data. The fluoroscopic data may be a fluoroscopic image, fluoroscopic images, or fluoroscopic video.

Additionally, the computing device may further enable navigation of a microwave ablation device to the target and activation of the microwave ablation device to ablate tissue proximate the target. Additionally, the computing device may further analyze the fluoroscopic data and determine whether device medical instrument is correctly positioned relative to the target. A second fluoroscopic data set of the first or second target may also be acquired from a second perspective relative to the patient such that a three-dimensional position of the medical instrument is viewable from a different angle. The second fluoroscopic data set may also be analyzed to determine whether the three-dimensional position of the medical instrument relative to the target tissue is correct, and if not, the three-dimensional position of the medical instrument relative to the target may be adjusted.

BRIEF DESCRIPTION OF THE DRAWINGS

Various aspects and embodiments of the present disclosure are described hereinbelow with references to the drawings, wherein.

DETAILED DESCRIPTION

The present disclosure is generally directed to addressing the navigational and location confirmatory shortcomings of the previously known navigation and fluoroscopic imaging confirmation methods and devices. According to one embodiment of the present disclosure, following navigation of a catheter to an area of interest, a fluoroscopic image (or series of fluoroscopic images) is captured. By registering the location of markers previously placed within the patient and captured in the fluoroscopic image to the location of markers which appear in 3D model data generated from a previously acquired CT image data set, the fluoroscopic image can be overlaid with data from the 3D model data including target location data, navigation pathway data, luminal network data and more.

Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
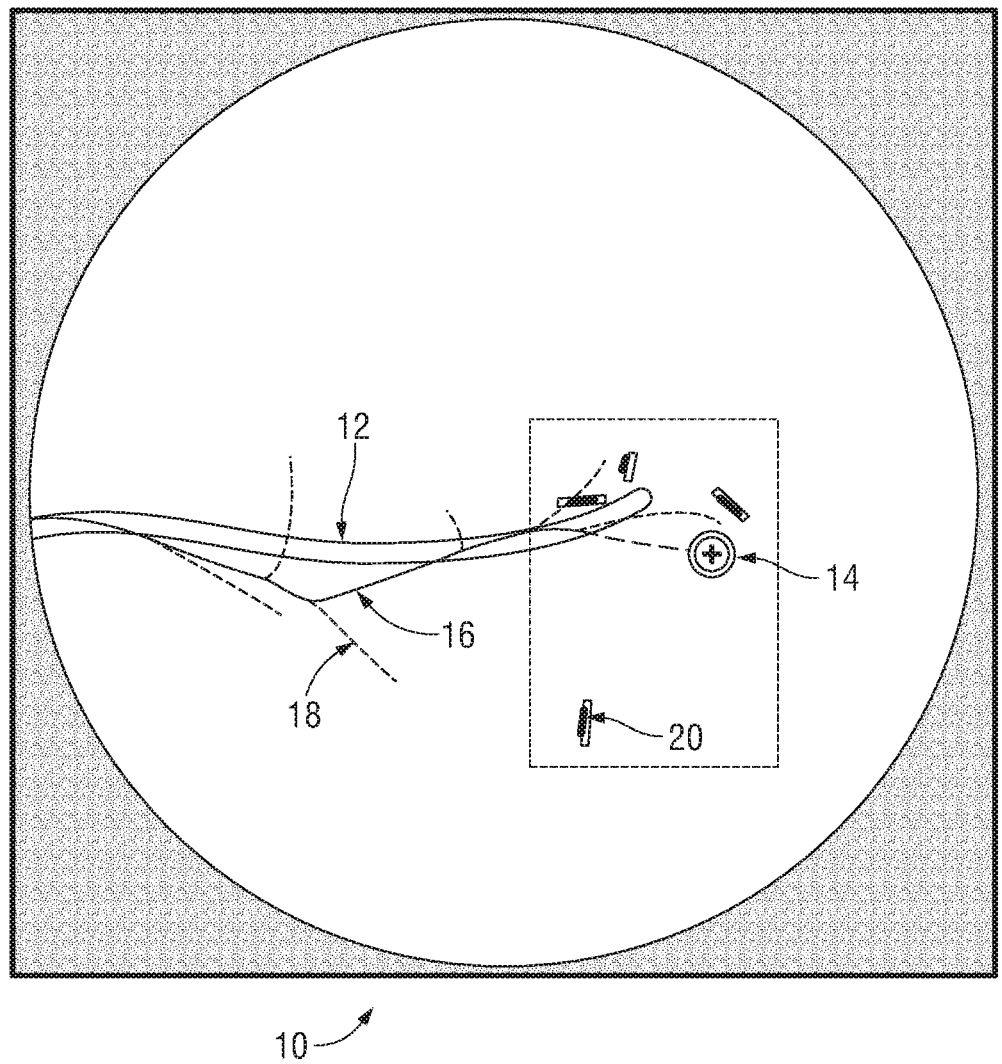
FIG. 1 depicts a portion of a user interface with navigational data from a navigation plan overlaid on a live fluoroscopic image.

FIG. 1 depicts the image outcome of one embodiment of the present disclosure. In FIG. 1, a composite fluoroscopic image 10 is displayed. The composite fluoroscopic image 10 may be presented on a display as an additional view of an Electromagnetic Navigation (EMN) system 100 (FIG. 2) used for navigation. Alternatively, the image may be presented on a fluoroscopic image viewer separate from the EMN system 100. The field of view of the fluoroscopic image 10 includes a distal portion of an extended working channel (EWC) 12 that has been maneuvered pursuant to a pathway plan, as will be described in greater detail below. The fluoroscopic image 10 is also overlaid with a variety of data originally developed and derived from navigation software. This additional data overlaid on the fluoroscopic image 10 includes a target 14, a pathway plan 16, luminal pathways of the area being imaged 18, and markers 20. With this enhanced fluoroscopic image 10 a clinician is allowed to visualize in real time the final placement of the EWC 12 in relation to the pathway plan 16, the target 14 and the markers 20 to ensure accurate final placement, as well as discern if there is any unintended movement of the EWC 12 as a result of tool exchanges into and out of the EWC 12.

Figure 2:
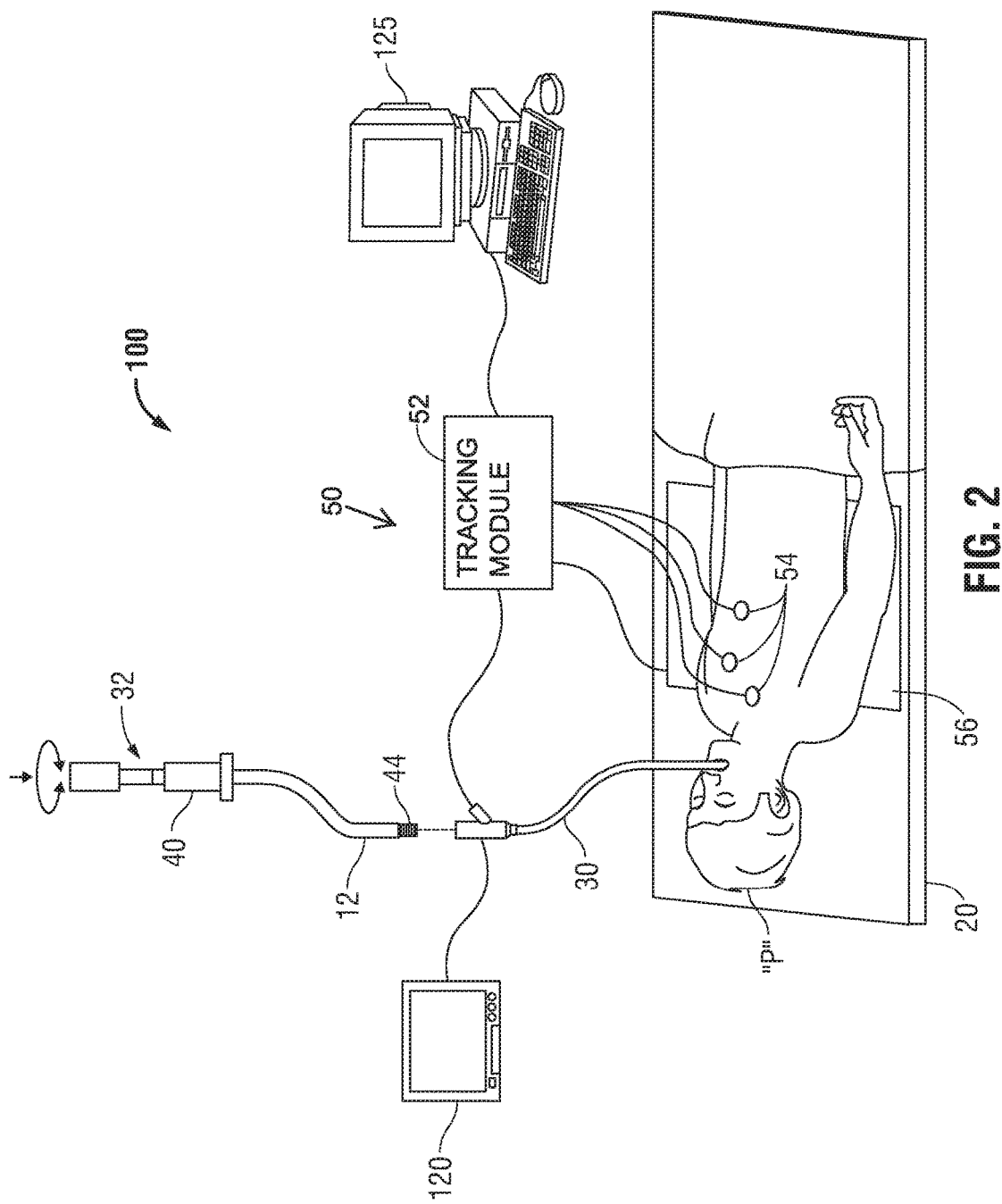
FIG. 2 is a perspective view of one illustrative embodiment of an electromagnetic navigation (EMN) system in accordance with the present disclosure.

FIG. 2 depicts an aspect of an EMN system 100 configured for reviewing CT image data to identify one or more targets 14, planning a pathway to an identified target 14 (planning phase), navigating an EWC 12 to the target 14 (navigation phase) via a user interface, and confirming placement of the EWC 12 relative to the target 14. One such EMN system is the ELECTROMAGNETIC NAVIGATION BRONCHOSCOPY® system currently sold by Covidien LP. The target 14 is a computer generated representation, created during the planning phase, of the tissue of interest identified by review of the CT image data. As described above, following navigation, a medical instrument such as a biopsy tool may be inserted into the EWC 12 to obtain a tissue sample from the tissue located at, or proximate to, the target 14.

As shown in FIG. 2, EWC 12 is part of a catheter guide assembly 40. In practice, the EWC 12 is inserted into bronchoscope 30 for access to a luminal network of the patient "P." Specifically, EWC 12 of catheter guide assembly 40 may be inserted into a working channel of bronchoscope 30 for navigation through a patient's luminal network. A locatable guide (LG) 32, including a sensor 44 is inserted into the EWC 12 and locked into position such that the sensor 44 extends a desired distance beyond the distal tip of the EWC 12. The position and orientation (6 DOF) of the sensor 44 relative to the reference coordinate system, and thus the distal end of the EWC 12, within an electromagnetic field can be derived. Catheter guide assemblies 40 are currently marketed and sold by Covidien LP under the brand names SUPERDIMENSION® Procedure Kits, or EDGE™ Procedure Kits, and are contemplated as useable with the present disclosure. For a more detailed description of the catheter guide assemblies 40, reference is made to commonly-owned U.S. patent application Ser. No. 13/836,203 filed on Mar. 15, 2013 by Ladtkow et al, and U.S. Pat. No. 7,233,820 the entire contents of both are hereby incorporated by reference.

EMN system 100 generally includes an operating table 20 configured to support a patient "P" a bronchoscope 30 configured for insertion through the patient's "P's" mouth into the patient's "P's" airways; monitoring equipment 120 coupled to bronchoscope 30 (e.g., a video display, for displaying the video images received from the video imaging system of bronchoscope 30); a tracking system 50 including a tracking module 52, a plurality of reference sensors 54, and a transmitter mat 56; a computing device 125 including software and/or hardware used to facilitate identification of a target 14, pathway planning to the target 14, navigation of a medical instrument to the target 14, and confirmation of placement of an EWC 12, or a suitable device therethrough, relative to the target 14.

Figure 3:
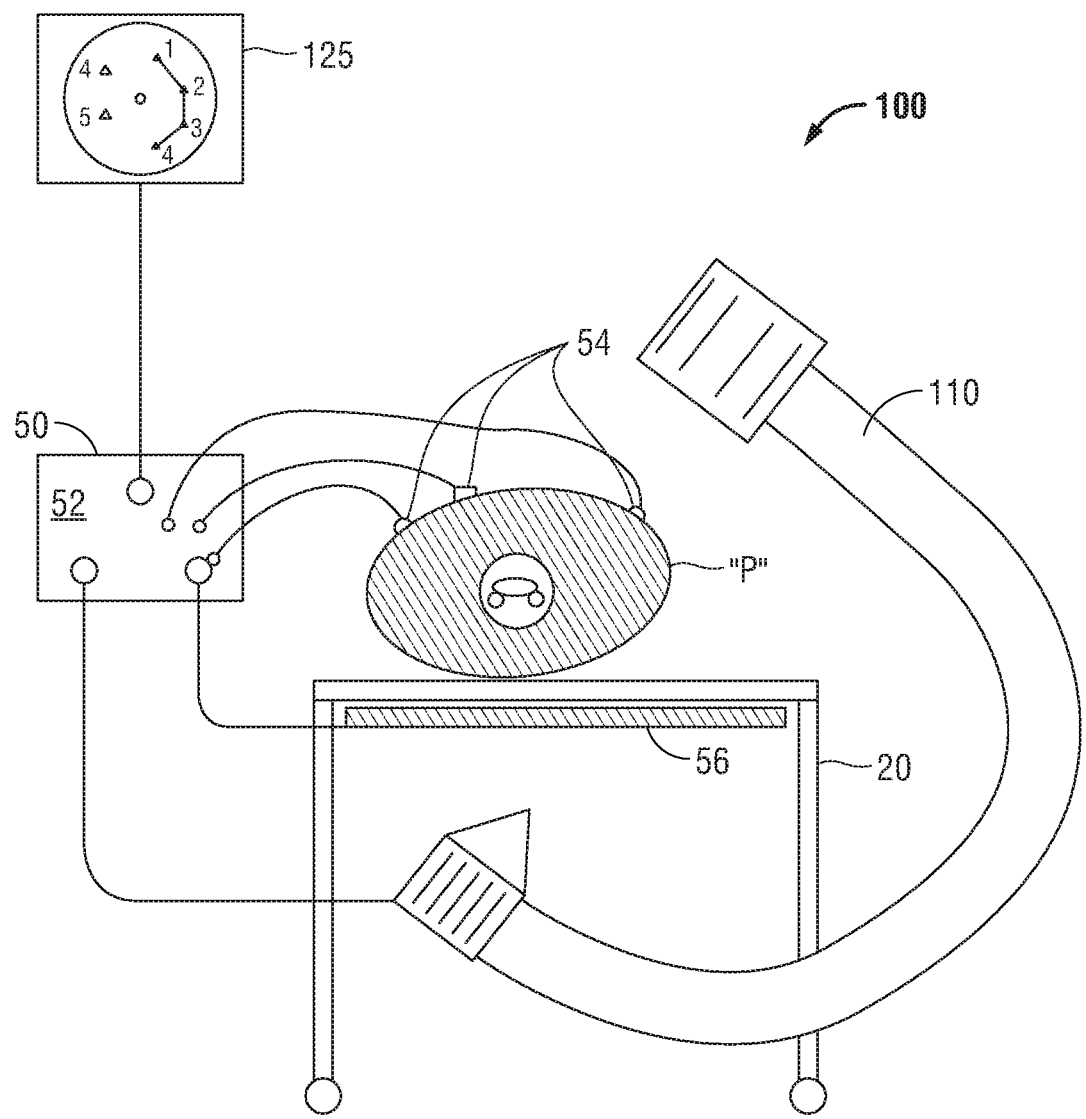
FIG. 3 is an end view of a fluoroscopic imaging C-arm incorporated in the EMN system of FIG. 2.

FIG. 3 depicts another view of the EMN system 100, including a fluoroscopic imaging device 110 capable of acquiring fluoroscopic or x-ray images or video of the patient "P." The images, series of images, or video captured may be stored within the imaging device 110 or transmitted to computing device 125 for storage, processing, and display. Additionally, the imaging device 110 may rotate about the patient "P" so that images may be acquired from different angles or perspectives relative to the patient "P." Imaging device 110 may include a single imaging device or more than one imaging device. In embodiments including multiple imaging devices, each imaging device may be a different type of imaging device or the same type. Further details regarding the imaging device 110 are described in U.S. Pat. No. 8,565,858, which is incorporated by reference in its entirety herein.

Computing device 125 may be any suitable computing device including a processor and storage medium, wherein the processor is capable of executing instructions stored on the storage medium. The computing device 125 may further include a database configured to store patient data, CT data sets including CT images, fluoroscopic data sets including fluoroscopic images and video, navigation plans, and any other such data. Although not explicitly illustrated, the computing device 125 may include inputs, or may otherwise be configured to receive, CT data sets and other data described herein. Additionally, computing device 125 includes a display configured to display graphical user interfaces such as those described below. Computing device 125 may be connected to one or more networks through which one or more databases may be accessed.

With respect to the planning phase, computing device 125 utilizes computed tomographic (CT) image data for generating and viewing a three-dimensional model of the patient's "P's" airways, enables the identification of a target 14 on the three-dimensional model (automatically, semi-automatically, or manually), and allows for determining a pathway through the patient's "P's" airways to tissue located at the target 14. More specifically, the CT scans are processed and assembled into a three-dimensional CT volume, which is then utilized to generate a three-dimensional model of the patient's "P's" airways. The three-dimensional model may be displayed on a display associated with computing device 125, or in any other suitable fashion. Using computing device 125, various views of the three-dimensional model or two-dimensional images generated from the three-dimensional model are presented. The three-dimensional model may be manipulated to facilitate identification of target 14 on the three-dimensional model or two-dimensional images, and selection of a suitable pathway through the patient's "'s" airways to access tissue located at the target 14 can be made. Once selected, the pathway plan, 3D model, and images derived therefrom can be saved and exported to a navigation system for use during the navigation phase(s). One such planning software is the ILOGIC® planning suite currently sold by Covidien LP.

With respect to the navigation phase, a six degrees-of-freedom electromagnetic tracking system 50, e.g., similar to those disclosed in U.S. Pat. Nos. 8,467,589, 6,188,355, and published PCT Application Nos. WO 00/10456 and WO 01/67035, the entire contents of each of which is incorporated herein by reference, or other suitable positioning measuring system, is utilized for performing registration of the images and the pathway and navigation, although other configurations are also contemplated. Tracking system 50 includes a tracking module 52, a plurality of reference sensors 54, and a transmitter mat 56. Tracking system 50 is configured for use with a locatable guide 32 and particularly sensor 44. As described above, locatable guide 32 and sensor 44 are configured for insertion through an EWC 12 into a patient's "P's" airways (either with or without bronchoscope 30) and are selectively lockable relative to one another via a locking mechanism.

As shown in FIGS. 2 and 3, transmitter mat 56 is positioned beneath patient "P." Transmitter mat 56 generates an electromagnetic field around at least a portion of the patient "P" within which the position of a plurality of reference sensors 54 and the sensor element 44 can be determined with use of a tracking module 52. One or more of reference sensors 54 are attached to the chest of the patient "P." The six degrees of freedom coordinates of reference sensors 54 are sent to computing device 125 (which includes the appropriate software) where they are used to calculate a patient coordinate frame of reference. Registration, as detailed below, is generally performed to coordinate locations of the three-dimensional model and two-dimensional images from the planning phase with the patient's "P's" airways as observed through the bronchoscope 30, and allow for the navigation phase to be undertaken with precise knowledge of the location of the sensor 44, even in portions of the airway where the bronchoscope 30 cannot reach. Further details of such a registration technique and their implementation in luminal navigation can be found in U.S. Patent Application Pub. No. 2011/0085720, the entire contents of which, is incorporated herein by reference, although other suitable techniques are also contemplated.

Registration of the patient "P's" location on the transmitter mat 56 is performed by moving LG 32 through the airways of the patient "P." More specifically, data pertaining to locations of sensor element 44, while locatable guide 32 is moving through the airways, is recorded using transmitter mat 56, reference sensors 54, and tracking module 52. A shape resulting from this location data is compared to an interior geometry of passages of the three-dimensional model generated in the planning phase, and a location correlation between the shape and the three-dimensional model based on the comparison is determined, e.g., utilizing the software on computing device 125. In addition, the software identifies non-tissue space (e.g., air filled cavities) in the three-dimensional model. The software aligns, or registers, an image representing a location of sensor 44 with a the three-dimensional model and two-dimensional images generated from the three-dimension model, which are based on the recorded location data and an assumption that locatable guide 32 remains located in non-tissue space in the patient's "P's" airways. Alternatively, a manual registration technique may be employed by navigating the bronchoscope 30 with the sensor 44 to pre-specified locations in the lungs of the patient "P", and manually correlating the images from the bronchoscope to the model data of the 3D model.

Following registration of the patient "P" to the image data and pathway plan, a user interface is displayed in the navigation software which sets forth the pathway that the clinician is to follow to reach the target 14. One such navigation software is the ILOGIC® navigation suite currently sold by Covidien LP.

Once EWC 12 has been successfully navigated proximate the target 14 as depicted on the user interface, the locatable guide 32 may be unlocked from EWC 12 and removed, leaving EWC 12 in place as a guide channel for guiding medical instruments including without limitation, optical systems, ultrasound probes, biopsy tools, ablation tools (i.e., microwave ablation devices), laser probes, cryogenic probes, sensor probes, and aspirating needles to the target 14.

Having described the components of system 100, depicted in FIGS. 2 and 3 the following description of FIGS. 4-7 provides an exemplary workflow of using the components of system 100 in conjunction with CT imaging to achieve the result depicted in FIG. 1. FIGS. 4-7, enable a method of identifying a target 14 and a pathway to the target 14 utilizing computed tomographic ("CT") images, and once identified, further enables the use of a navigation or guidance system to position the EWC 12 of a catheter guide assembly 40, and medical instrument positioned therethrough, relative to the target 14. In addition, the following enables accurate live image confirmation of the location of the EWC 12 prior, during, and after treatment. CT image data facilitates the identification of a target 14, planning of a pathway to an identified target 14, as well as providing the ability to navigate through the body to the target 14 via a user interface. This includes a preoperative component and an operative component (i.e., pathway planning and pathway navigation) as will be described in further detail below. Live fluoroscopic visualization of the placement of the EWC 12 and/or medical instruments positioned therethrough, relative to the target 14 is enabled, thus enabling the clinician to actually see the proper placement of the device relative to the target 14 in real time using a combination of live fluoroscopic data and the CT image data (or selected portions thereof). Once placement of the medical instrument/EWC 12 is confirmed within the target 14, a surgical treatment or diagnostic sampling may be performed. For example, microwave energy can be transmitted to an ablation device positioned through EWC 12 to treat tissue located at the target 14.

Following treatment of tissue located at the target 14, the live fluoroscopic imaging may be utilized to confirm, for example, that a suitable ablation zone has been formed around the tissue and whether additional application of energy is necessary. These steps of treating and imaging may be repeated iteratively until a determination is made that the tissue located at the target 14 has been successfully treated. Moreover, the methodology described above using the imaging modalities to confirm the extent of treatment and determine whether additional application of energy is necessary can be combined with the radiometry and temperature sensing techniques to both confirm what is depicted by the imaging modality and to assist in determining treatment cessation points.

Turning now to FIGS. 4-7, methods for performing enhanced navigation using system 100 will now be described with particular detail. Although the methods illustrated and described herein are illustrated and described as being in a particular order and requiring particular steps, any of the methods may include some or all of the steps and may be implemented in any order not specifically described.

Figure 4:
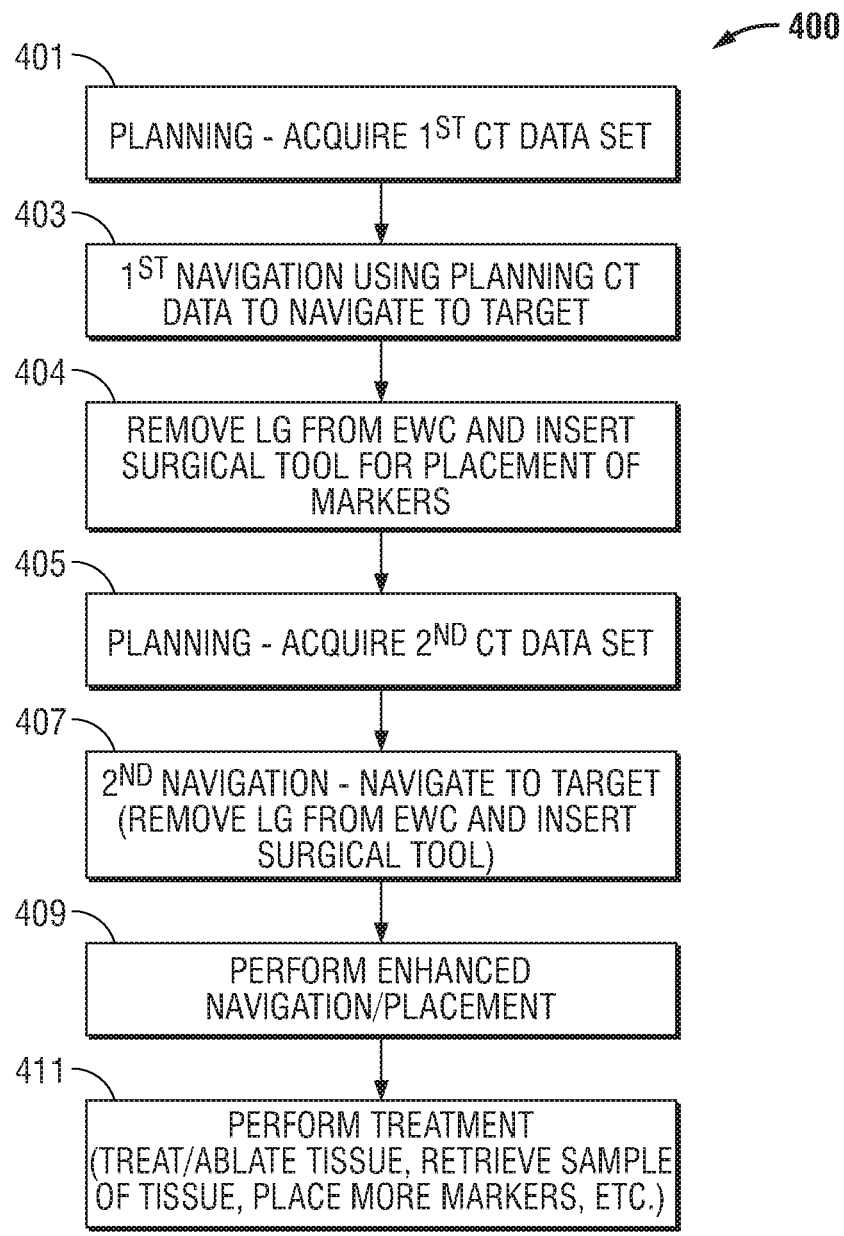
FIG. 4 is a flow chart of a method for performing a procedure with enhanced navigation using the system of FIG. 3 in accordance with the instant disclosure.

With particular reference to FIG. 4, a method for performing enhanced navigation is illustrated and will be described as method 400. Method 400 begins with the pathway planning step 401. In embodiments, the pathway planning step 401 includes acquiring a first set of CT images for generation of a first CT data set. However, the acquisition of the CT images and/or the generating of the CT data set may be completed prior to the pathway planning step 401 in which the pre-acquired CT data set is uploaded into system 100. In embodiments, the pathway planning step 401 includes three general steps. The first step involves using software for generating and viewing a three-dimensional model of the bronchial airway tree ("BT") and viewing the CT data to identify targets (i.e., target 14). The second step involves using the software for selection of a pathway on the BT to the identified target 14, either automatically, semi-automatically, or manually, if desired. Optionally, the pathway may be automatically segmented into a set of waypoints along the path that can be visualized on a display. In embodiments, a third step may include confirmation of the plan using a fly-through view, and then exporting the pathway plan for use in a navigation system. It is to be understood that the airways are being used herein as an example of a branched luminal network. Hence, the term "BT" is being used in a general sense to represent any such luminal network (e.g., the circulatory system, or the gastro-intestinal tract, etc.). Further details regarding the planning step are described in U.S. patent application Ser. No. 13/838,805, filed Mar. 15, 2013, the entire contents of which are incorporated by reference herein.

Method 400 then proceeds to a first navigation step 403. In step 403, using the plan developed in step 401, an EWC 12 is navigated to a target 14. Specifically, with reference back to FIGS. 1-3, the plan developed in step 401 is imported into computing device 125, or generated by computing device 125, and the plan is registered with the patient's "P's" location enabling a clinician to follow the plan within the patient's "P's" BT with EWC 12 and LG 32. A clinician follows the plan by advancing the bronchoscope 30, and once the bronchoscope 30 is wedged, advancing the EWC 12 of the catheter guide assembly 40 through the working channel of the bronchoscope 30 to the target 14. The location of the distal end of the EWC 12, where the LG 32 is located, is monitored by the tracking system 50 as it is advanced through the BT. Further details regarding the navigation are described in U.S. Pat. No. 7,233,820, the entire contents of which are hereby incorporated by reference in its entirety.

After navigating the EWC 12 proximate the target 14 (via the user interface), in 404 the EWC 12 is used in conjunction with marker placement tools and biopsy tools to place markers 20 in tissue located around the target 14 and, optionally, for the retrieval of biopsy samples of the tissue proximate target 14. As understood by those of skill in the art, and as described above, the target 14 is a computer generated representation, created during the planning phase, of the tissue of interest identified by review of the CT image data. Thus, markers are placed in, and biopsy samples may be taken from, the tissue of the patient "P" at the location the navigation system identifies as corresponding to the location of the target 14 in the pathway plan.

After the markers 20 are placed, the medical instrument used to place the markers 20, along with the EWC 12, is removed from the patient's "P's" BT and the method proceeds to step 405 where a second set of CT images is acquired for generating a second CT data set. The second CT data set acquired in step 405 includes CT images of the patient "P" including the markers 20 placed in step 404. This may be performed immediately or following cytopathologic examination of the biopsy samples.

Following acquisition of the second CT image set, analysis of any biopsy samples taken, and confirming that either further biopsy or treatment is necessary, a new pathway plan is developed by the clinician and a second navigation step 407 is performed including navigating to the target 14 using a pathway plan generated using the second CT data. This second pathway plan may selectively include data from the navigation plan generated in step 401 using the first CT data set. In step 407, the EWC 12 is navigated to the target 14 in a similar manner as the first navigation step 403 and therefore will not be described in further detail.

Subsequent to navigating the EWC 12 to the target 14 in step 407, method 400 proceeds to step 409 to perform enhanced medical imaging and device placement. Specifically, after the EWC 12 is navigated to the target 14 in step 407, the LG 32 may again be removed from the EWC 12 and a medical instrument may be positioned proximate the target 14 via the EWC 12. Fluoroscopic imaging is undertaken and a composite fluoroscopic image 10 (FIG. 1) including data from the pathway plan data is displayed to the clinician. Step 409 enables a clinician to verify the position of the medical instrument relative to the target 14 and make adjustments to the position of the surgical device relative to the target 14 before performing a surgical procedure (i.e., retrieval of sample tissue, ablation of tissue, placement of additional markers). Details with respect to enhanced medical device placement of step 409 will be described in further detail below with respect to method 500 in FIG. 5. Subsequent to performing the enhanced medical imaging device placement in step 409, method 400 proceeds to step 411 where the medical instrument, properly positioned relative to the target 14 is used for its intended purposes (i.e., a microwave ablation device is activated to treat tissue, a biopsy tool retrieves a sample of tissue, a marker placement tool places the marker(s)).

Figure 5:
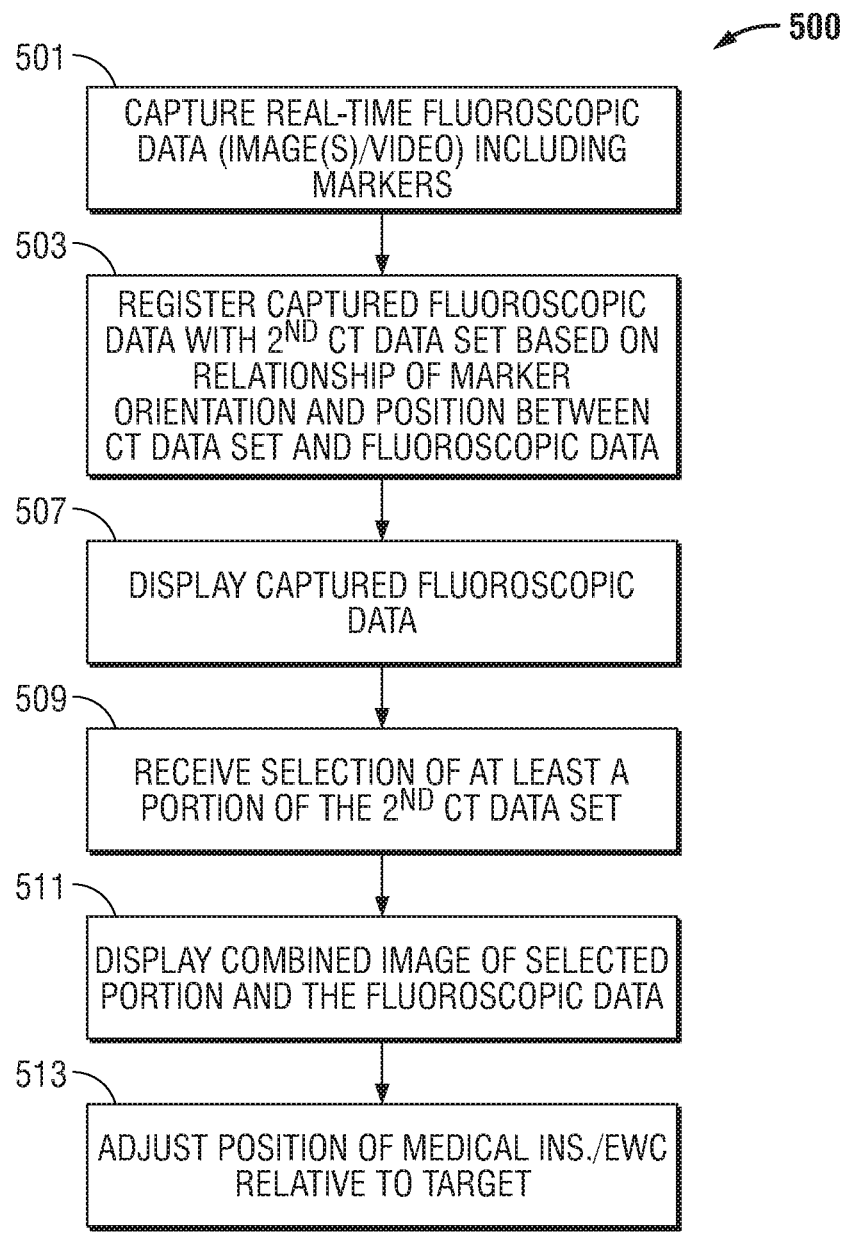
FIG. 5 is a flow chart of a method for performing enhanced navigation using the system of FIG. 3 in accordance with the instant disclosure.

Turning now to FIG. 5 and with reference to FIGS. 1-3, a method for performing enhanced navigation will be described in particular detail and will be referred to as method 500. Method 500 begins at step 501 after the EWC 12 is navigated to the target 14 following the second navigating step 407 of method 400 (FIG. 4). Method 500 may be used to confirm placement of the EWC 12, or any medical instrument positioned through the EWC 12, relative to the target 14 to verify and adjust its position relative to the target 14 prior to performing a surgical procedure (i.e., retrieving a sample of the target tissue, ablating the target tissue).

Figure 6:
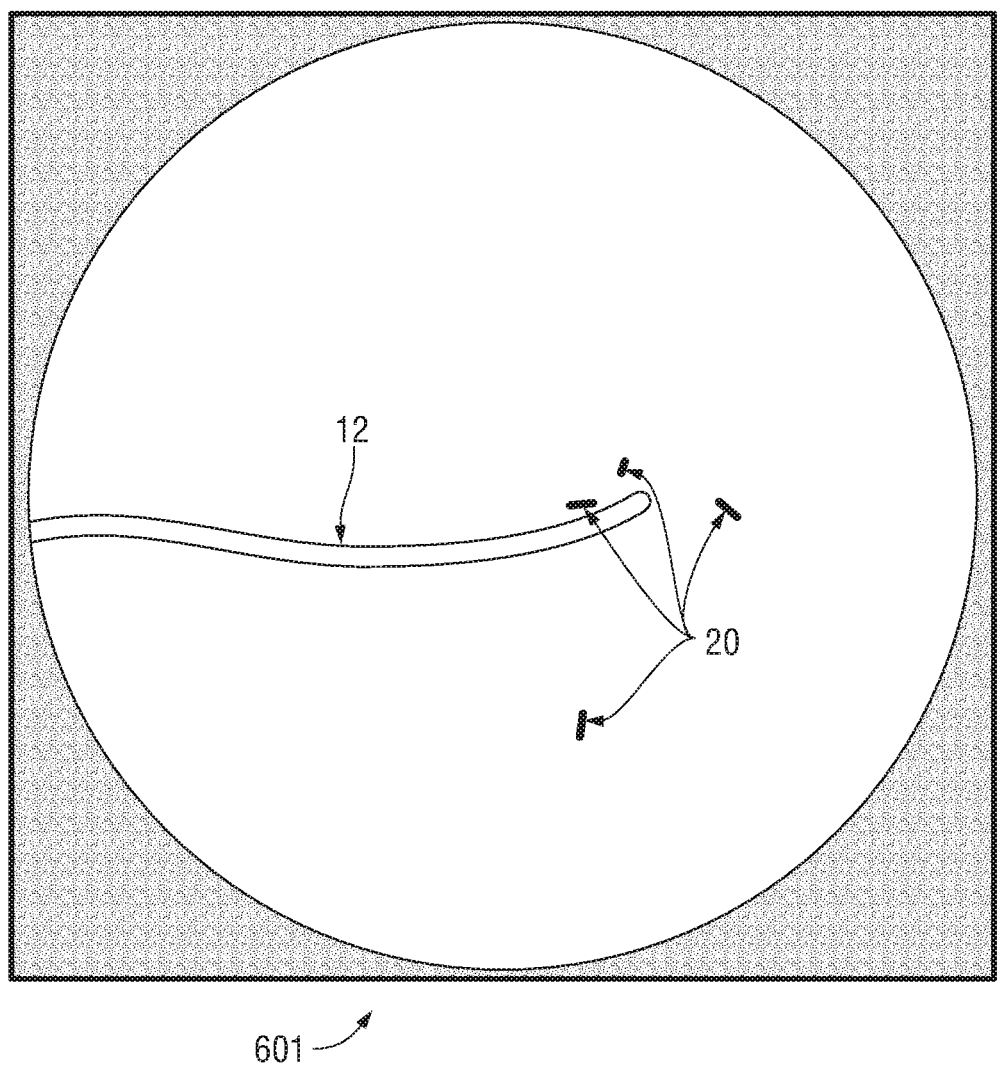
FIG. 6 is an illustration of an example fluoroscopic image/video captured by a C-arm showing markers and an extended working channel of a catheter assembly positioned within a target region of a patient in accordance with the instant disclosure.

In step 501, a real-time fluoroscopic image of the patient "P" is captured. FIG. 6 illustrates an example of a real-time fluoroscopic image 601 captured in step 501. The real-time fluoroscopic image 601 is captured using the imaging device 110 (FIG. 3). As seen in FIG. 6, the markers 20 placed in the proximity of the target 14 (step 404 of method 400) and the EWC 12 previously navigated to the target 14 in the pathway plan (step 407 of method 400) are visible in the captured fluoroscopic image 601. In embodiments, step 501 includes capturing a series of fluoroscopic images of the target region and/or a live fluoroscopic video stream.

In step 503 the fluoroscopic image 601 captured in step 501 is registered with the second CT data set acquired in step 405 of method 400. In embodiments, the registration of the fluoroscopic image 601 and the second CT data set is based on a comparison of the position and orientation of the markers 20 within the fluoroscopic image 601 and the position and orientation of the markers 20 within the second CT data set (not shown). Specifically, computing device 125 detects markers 20 in the CT images of the second CT data set using methods such as intensity thresholding or via clinician manual identification. Possible false indicators such as from calcification or other metal objects visible in the CT images may be detected and disregarded. In embodiments, the second CT data set may be displayed for a clinician to identify the markers 20 on a graphical user interface. Additionally, in step 503, the computing device 125 detects the markers 20 depicted in the fluoroscopic image(s) 601 acquired in step 501. For marker 20 detection in the fluoroscopic image(s) 601, computing device 125 may employ techniques such as contrast detection, intensity detection, shape detection, minimum axis detection, and/or any combinations thereof. Additionally, computing device 125 may also detect the marker center and marker end points for each marker 20 detected. After detecting the markers 20 in the fluoroscopic image 601 acquired in step 501 and the CT data set stored in computing device 125, computing device 125 then registers the fluoroscopic image 601 with the CT data set by comparing one or more of the position, length, angle, orientation, and distance between each of the markers 20 or between all of the markers 20 with the CT data set.

In step 507, the fluoroscopic image(s) 601 and/or video captured in step 501 is displayed on the display of computing device 125.

In step 509, computing device 125 analyzes the position and/or orientation of the markers 20 depicted in the fluoroscopic image 601 and performs a mathematical calculation to identify a 2D slice of the 3D model generated from the second CT data set such that one or more of the position, length, angle, orientation, and distance between each of the markers 20 or between all of the markers 20 in the identified 2D slice correspond with the same factors in the fluoroscopic image. This may be performed in conjunction with position and/or orientation data received from the imaging device 110. Once the 2D image from the CT data set corresponding to the fluoroscopic image is ascertained, the clinician may selectively identify what portions of the data included on the 2D image to incorporate into the displayed fluoroscopic image 601.

Alternatively, data from the fluoroscopic image 601 may be incorporated into the 2D image from the CT data set. As an example, the target 14 which was identified in the CT data set during the planning phase may be available for selection. In addition, the pathway 16 and luminal network 18, as well as other data from the CT data set may be available for selection. As a result, a clinician may select an object that is viewable in a CT image of the CT data set that is not viewable in the fluoroscopic image 601 (i.e., a portion of soft tissue), such that the selection may be combined with the fluoroscopic image 601 to create a combined image 10 (FIG. 1).

In addition to permitting selection, the computing device 125 may also output an indicator of resolution of the markers 20 from the fluoroscopic image in the CT data set. For example, in FIG. 1 each marker 20 is circumscribed by a line indicating that it has been positively identified. If markers 20 are not resolved in the CT data set, this may be an indicator that the 2D image and the fluoroscopic image 601 are not actually registered to one another, and provides an indicator to the clinician that they may wish to perform another fluoroscopic imaging before proceeding.

In step 511, with reference with FIG. 1, the combined or composite image 10 is displayed on the display of computing device 125 and/or another device. The combined image 10 displayed in step 511 includes the portion selected in step 509 (e.g., the target 14) and the fluoroscopic image(s) 601 (FIG. 6) or video displayed in step 507. The combined image 10 may be a fused image, an overlay of images, or any other display of multiple images and/or video known in the art. For example, as illustrated in FIG. 1, where a user selects the target 14 in an image of the CT data in step 509 (or when the target 14 is automatically selected in step 509), in step 511 the combined image 10 includes the fluoroscopic image 601 (FIG. 6) (including visibility of the markers 20 and EWC 12 as well as any medical instrument, placed therein) and the selection of the image of the CT data set (the target 14). Using the registration between the fluoroscopic image(s) 601 and/or video and the CT data set in step 503, the system 100 determines where the selected portion (e.g., target 14) is to be positioned (i.e., overlay, fused, etc.) within the fluoroscopic image 601 and/or video to create the combined image 10.

In step 513, the position of the EWC 12, or the medical instrument positioned within the EWC 12, is adjusted relative to the target 14 and displayed using the combined image 10 generated in step 511. Further details regarding the adjustment in step 511 will be described in further detail below with reference to FIG. 7.

Figure 7:
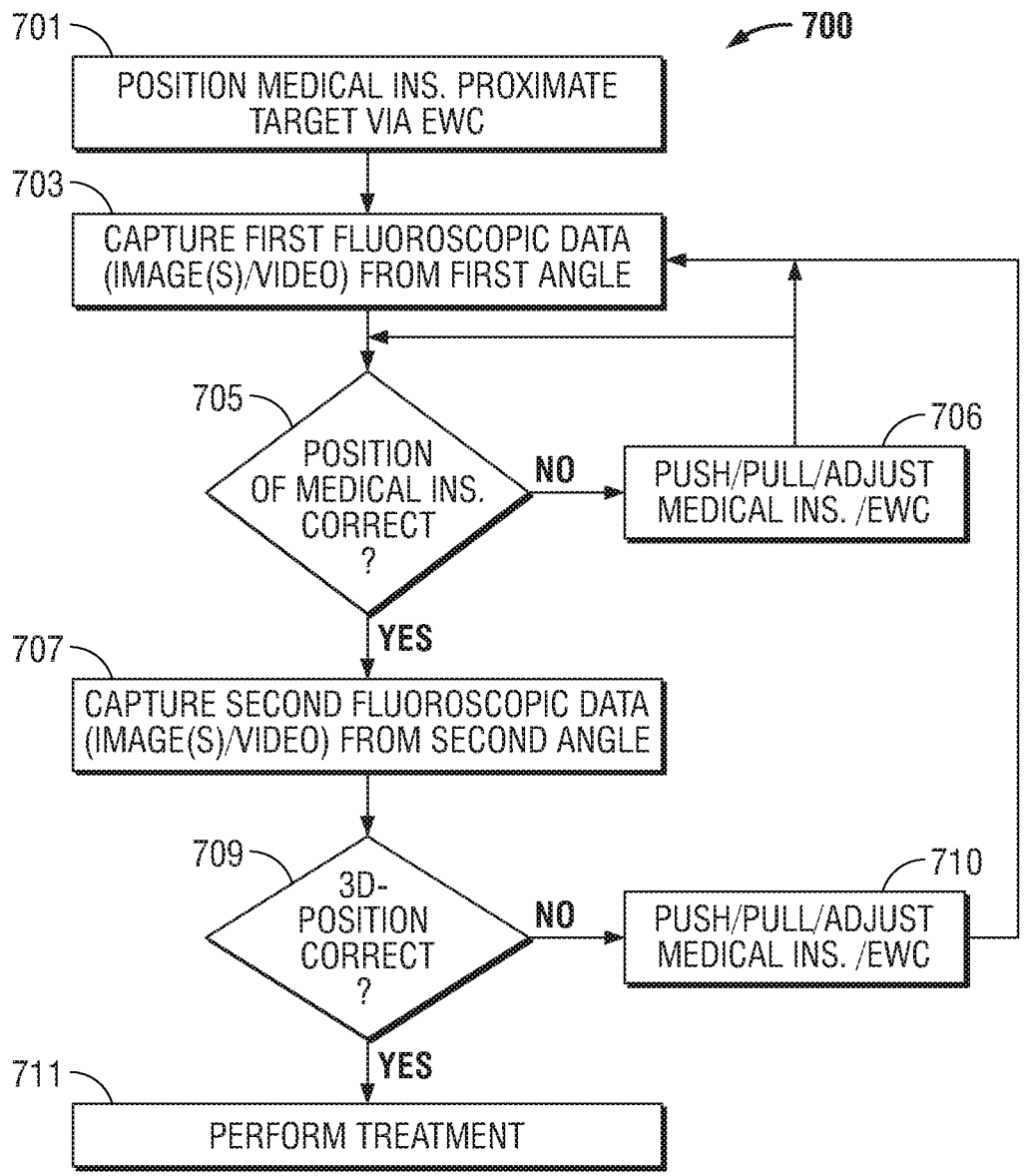
FIG. 7 is a flow chart of a method for adjusting the position of a medical instrument relative to a target in accordance with the instant disclosure.

Turning now to FIG. 7, a method for adjusting the position/placement of the EWC 12, or the medical instrument positioned therein, will now be described and referred to as method 700. After navigating the EWC 12 to the target 14, in order to ensure that the medical instrument positioned within the EWC 12 of the catheter guide assembly 40 is properly positioned relative to the target 14, using method 700 a clinician can ensure that the medical instrument is properly positioned or otherwise adjust the position of the medical instrument relative to the target 14 until it is properly positioned. Method 700 begins at step 701 where a medical instrument is positioned relative to a target 14 via the EWC 12.

In step 703, using imaging device 110, a fluoroscopic image/video is captured from a first angle. The fluoroscopic image/video captured in step 703 is transmitted to computing device 125 for display on a graphical user interface and for the generation of a combined image 10 (FIG. 1). Viewing the combined image 10, which displays both the target 14 and the medical instrument in real-time relative to the target 14, a clinician may determine whether the position of the medical instrument relative to the target 14 is correct (step 705). If the position of the medical instrument relative to the target 14 is correct (yes in step 705) then method 700 proceeds to step 706. Alternatively, if the position of the medical instrument is not correct (no in step 705), then method 700 proceeds to step 706.

In step 706, a clinician adjusts the position of the medical instrument by manipulating the catheter guide assembly 40 and therewith the EWC 12 and any medical instrument located therein. If the imaging device 110 is capturing a live video, then the adjustment of the medical instrument/EWC 12 in step 706 is viewed in real time on the display of computing device 125 or any other suitable devices. However, if the imaging device 110 is only capturing an image, then a method 700 reverts back to step 703 where a new fluoroscopic image is captured displaying the new/adjusted position of the medical instrument/EWC 12. This process is repeated until the position of the medical instrument/EWC 12 is correct (yes in step 705). Once the position of the EWC 12 is correct (yes in step 705), then method 700 proceeds to step 707.

In step 707, a second fluoroscopic image/video is captured from a second angle relative to the patient. That is, the imaging device 110 is moved to a new location such that a second fluoroscopic image/video may be captured from a different viewing angle. The fluoroscopic image/video captured in step 707 is transmitted to computing device 125 for display on a graphical user interface and for the generation of the combined image 10 (FIG. 1). Viewing the combined image 10, which displays both the target 14 and the medical instrument in real-time relative to the target 14, a clinician may determine whether the three-dimensional position of the medical instrument relative to the target 14 is correct (step 709). If the three-dimensional position the medical instrument relative to the target 14 is correct (yes in step 709), then method 700 proceeds to step 711. Alternatively, if the three-dimensional position of the medical instrument is not correct (no in step 709), then method 700 proceeds to step 710.

In step 710, the clinician adjusts the three-dimensional position of the medical instrument relative to the target 14 by pushing/pulling the catheter guide assembly 40 and therewith the EWC 12 and any medical instrument located therein relative to the target 14. Because of the adjustment of the three-dimensional position of the medical instrument/ EWC 12, a clinician may wish to revert back to step 703 to view the position of the medical instrument/EWC 12 relative to the target 14 again from the first angle.

Once the three-dimensional position of the medical instrument/EWC 12 relative to the target 14 is correct (yes in step 709), method 700 proceeds to step 711 where the treatment is performed. As described above, depending on the intended treatment to be performed, the treatment may include retrieving samples of tissue for biopsy or testing, ablating tissue located at the target 14, placing markers 20 or any other suitable surgical procedure.

From the foregoing and with reference to the various figure drawings, those skilled in the art will appreciate that certain modifications can also be made to the present disclosure without departing from the scope of the same. For example, one or modifications may be made in the way of device delivery and placement; device cooling and antenna buffering; and sensor feedback.

As can be appreciated a medical instrument such as a biopsy tool or an energy device, such as a microwave ablation catheter, that is positionable through one or more branched luminal networks of a patient to treat tissue may prove useful in the surgical arena and the present disclosure is directed to such apparatus, systems, and methods. Access to luminal networks may be percutaneous or through natural orifice. In the case of natural orifice, an endobronchial approach may be particularly useful in the treatment of lung disease. Targets, navigation, access and treatment may be planned pre-procedurally using a combination of imaging and/or planning software. In accordance with these aspects of the present disclosure, the planning software may offer custom guidance using pre-procedure images. Navigation of the luminal network may be accomplished using image-guidance. These image-guidance systems may be separate or integrated with the energy device or a separate access tool and may include MRI, CT, fluoroscopy, ultrasound, electrical impedance tomography, optical, and/or device tracking systems. Methodologies for locating the access tool include EM, IR, echolocation, optical, and others. Tracking systems may be integrated to an imaging device, where tracking is done in virtual space or fused with preoperative or live images. In some cases the treatment target may be directly accessed from within the lumen, such as for the treatment of the endobronchial wall for COPD, Asthma, lung cancer, etc. In other cases, the energy device and/or an additional access tool may be required to pierce the lumen and extend into other tissues to reach the target, such as for the treatment of disease within the parenchyma. Final localization and confirmation of energy device placement may be performed with imaging and/or navigational guidance using the modalities described below. The energy device has the ability to deliver an energy field for treatment (including but not limited to electromagnetic fields).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for enhanced surgical navigation comprising:
a computing device configured to:
   import a navigation path generated from a first data set of computed tomography images of a branched luminal network previously acquired, the navigation path defining a route to be followed through the branched luminal network to a target;
   display the route of the navigation path on a graphical user interface for a first navigation to the target by following the route and for placement of a plurality of markers in tissue proximate the target;
   acquire a second data set of computed tomography images of the branched luminal network including the plurality of markers;
   generate a three-dimensional model of the branched luminal network from the second data set of computed tomography images; and
   generate a second navigation path through the branched luminal network using the three-dimensional model generated, the second navigation path defining a second route to be followed through the branched luminal network to the target for a second navigation to the target; and
an imaging device configured to capture fluoroscopic data of tissue proximate the plurality of markers,
wherein the computing device is further configured to:
   register the fluoroscopic data to the second data set of computed tomography images; and
   create a composite fluoroscopic image including:
      the fluoroscopic data;
      an object derived from the second data set of computed tomography images; and
      a representation of the branched luminal network derived from the second data set of computed tomography images.

2. The system according to claim 1, wherein the computing device is further configured to display the composite fluoroscopic image on a second graphical user interface to enable navigation of a medical instrument to tissue proximate the target using the composite fluoroscopic image.

3. The system according to claim 1, wherein the composite fluoroscopic image further includes a representation of the second route of the second navigation path through the branched luminal network from the second data set of the computed tomography images.

4. The system according to claim 1, wherein the computing device is further configured to:
  display a representation of the second data set of computed tomography images on a second graphical user interface; and
  display the fluoroscopic data on the second graphical user interface.

5. The system according to claim 1, wherein the computing device is further configured to:
  receive a selection of at least a portion of the second data set of computed tomography images or the fluoroscopic data; and
  combine the selection with at least one of the second data set of computed tomography images or the fluoroscopic data into the composite fluoroscopic image.

6. The system according to claim 1, wherein the composite fluoroscopic image includes at least one of a fused, superimposed, or overlaid image of at least a portion of the second data set of computed tomography images with the fluoroscopic data.

7. The system according to claim 1, wherein the fluoroscopic data includes a medical instrument positioned relative to tissue proximate the target and the computing device is further configured to:
  analyze the composite fluoroscopic image and determine whether the medical instrument is correctly positioned relative to the target.

8. The system according to claim 7, wherein the computing device is further configured to:
  acquire a second fluoroscopic data set of tissue proximate the plurality of markers from the imaging device from a second perspective such that a three-dimensional position of the positioned medical instrument is viewable from a different angle; and
  analyze the second fluoroscopic data set to determine whether the three-dimensional position of the positioned medical instrument relative to the target is correct.

9. The system according to claim 1, wherein the fluoroscopic data is real-time fluoroscopic video of tissue proximate the plurality of markers.

10. The system according to claim 1, further comprising a second imaging device configured to capture a second fluoroscopic data from a different perspective than the fluoroscopic data.

11. The system according to claim 1, wherein the fluoroscopic data is at least one fluoroscopic image of tissue proximate the plurality of markers.

12. The system according to claim 1, further comprising a catheter guide assembly navigatable to the target using the navigation path, the catheter guide assembly including an extended working channel insertable into a working channel of a bronchoscope to access a luminal network.

13. The system according to claim 12, further comprising a biopsy device positionable through the extended working channel.

14. The system according to claim 12, further comprising a microwave ablation device positionable through the extended working channel.

15. The system according to claim 1, wherein the computing device is configured to register the fluoroscopic data to the second data set of computed tomography images based on a position and orientation of at least one of the plurality of markers.

16. The system according to claim 1, wherein the computing device is configured to:
  identify a slice of the second data set of computed tomography images having a marker position and orientation corresponding to a marker position and orientation within the fluoroscopic data; and
  register the fluoroscopic data to the second data set of computed tomography images based on the identified slice.

* * * * *